(12) United States Patent
Basu et al.

(10) Patent No.: US 9,907,480 B2
(45) Date of Patent: Mar. 6, 2018

(54) CATHETER SPINE ASSEMBLY WITH CLOSELY-SPACED BIPOLE MICROELECTRODES

(71) Applicant: Biosense Webster (Israel) Ltd., Yokneam (IL)

(72) Inventors: Shubhayu Basu, Anaheim, CA (US); Mario A. Solis, Rancho Cucamonga, CA (US)

(73) Assignee: Biosense Webster (Israel) Ltd., Yokneam, IL (US)

( * ) Notice: Subject to any disclaimer, the term of this patent is extended or adjusted under 35 U.S.C. 154(b) by 0 days.

(21) Appl. No.: 15/018,810

(22) Filed: Feb. 8, 2016

(65) Prior Publication Data
US 2017/0224237 A1    Aug. 10, 2017

(51) Int. Cl.
  *A61B 5/042* (2006.01)
  *A61M 25/00* (2006.01)
  *A61B 18/14* (2006.01)

(52) U.S. Cl.
  CPC ............ *A61B 5/0422* (2013.01); *A61B 5/042* (2013.01); *A61B 18/1492* (2013.01); *A61M 25/0054* (2013.01); *A61M 25/0067* (2013.01)

(58) Field of Classification Search
  CPC .................................................. A61B 5/0422
  See application file for complete search history.

(56) References Cited

U.S. PATENT DOCUMENTS

| 6,123,699 A | 9/2000 | Webster, Jr. |
| 6,171,277 B1 | 1/2001 | Ponzi |
| 6,183,435 B1 | 2/2001 | Bumbalough et al. |
| 6,183,463 B1 | 2/2001 | Webster, Jr. |
| 6,198,974 B1 | 3/2001 | Webster, Jr. |
| 6,210,407 B1 | 4/2001 | Webster |
| 6,267,746 B1 | 7/2001 | Bumbalough |
| 8,603,069 B2 | 12/2013 | Selkee |
| 9,314,299 B2 * | 4/2016 | Fang ................... A61B 5/0422 |
| 2009/0143651 A1 * | 6/2009 | Kallback ............ A61B 5/02007 600/301 |

* cited by examiner

*Primary Examiner* — Lee S Cohen
(74) *Attorney, Agent, or Firm* — Lewis Roca Rothgerber Christie LLP

(57) ABSTRACT

An electrophysiologic catheter with a distal electrode assembly carrying very closely-spaced bipole microelectrodes on a plurality of divergent spines that can flexibly spread over tissue surface area minimized detection of undesirable noise, including far-field noise. Each spine has a flexible microelectrode panel having a substrate, at least one pair of microelectrodes, a trace for each microelectrode, and a soldering pad. Adjacent microelectrodes of a bipole pair are separated by a space gap distance ranging between about 50-300 microns. Each microelectrode may have a width of about 200 or 300 microns.

20 Claims, 10 Drawing Sheets

CATHETER SPINE ASSEMBLY WITH CLOSELY-SPACED BIPOLE MICROELECTRODES

FIELD OF INVENTION

This invention relates to an electrophysiology catheter, in particular, a cardiac electrophysiology catheter with an electrode configuration that provides for more accurate and discrete sensing of fractionated signals.

BACKGROUND

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Once the catheter is positioned within the heart, the location of aberrant electrical activity within the heart is then located.

One location technique involves an electrophysiological mapping procedure whereby the electrical signals emanating from the conductive endocardial tissues are systematically monitored and a map is created of those signals. By analyzing that map, the physician can identify the interfering electrical pathway. A conventional method for mapping the electrical signals from conductive heart tissue is to percutaneously introduce an electrophysiology catheter (electrode catheter) having mapping electrodes mounted on its distal extremity. The catheter is maneuvered to place these electrodes in contact with the endocardium. By monitoring the electrical signals at the endocardium, aberrant conductive tissue sites responsible for the arrhythmia can be pinpointed.

For sensing by ring electrodes mounted on a catheter, lead wires transmitting signals from the ring electrodes are electrically connected to a suitable connector in the distal end of the catheter control handle, which is electrically connected to an ECG monitoring system and/or a suitable 3-D electrophysiology (EP) mapping system, for example, CARTO, CARTO XP or CARTO 3, available from Biosense Webster, Inc. of Irwindale, Calif.

The closely-spaced electrode pairs allow for more accurate detection of near-field potentials versus far-field signals, which can be very important when trying to treat specific areas of the heart. For example, near-field pulmonary vein potentials are very small signals whereas the atria, located very close to the pulmonary vein, provides much larger signals. Accordingly, even when the catheter is placed in the region of a pulmonary vein, it can be difficult for the electrophysiologist to determine whether the signal is a small, close potential (from the pulmonary vein) or a larger, farther potential (from the atria). Closely-spaced bipoles permit the physician to more accurately remove far field signals and obtain a more accurate reading of electrical activity in the local tissue. Accordingly, by having closely-spaced electrodes, one is able to target exactly the locations of myocardial tissue that have pulmonary vein potentials and therefore allows the clinician to deliver therapy to the specific tissue. Moreover, the closely-spaced electrodes allow the physician to determine the exact anatomical location of the ostium/ostia by the electrical signal.

However, manufacturing and assembling catheters with closely and precisely spaced ring electrodes pose many challenges. Accuracy and consistency in spacing between adjacent electrodes become critical to catheter manufacturing and assembly. Conventional methods often use adhesives such as polyurethane to seal each ring electrode, which creates a margin between adjacent electrode or electrode pairs that can limit how closely the electrodes can be spaced from each other. Typically, spacing of 1.0 mm or larger between electrode pairs can be achieved using such conventional methods. However, spacing smaller, especially 0.2 or 0.1 mm spacing is difficult to achieve. With such smaller spacing, there is the risk of adjacent electrodes coming in contact due to electrode tolerance specification or shifting of electrodes during assembly when medical grade adhesive such as Polyurethane is applied or when medical epoxy is curing.

Moreover, the conventional methods of attaching a lead wire to a ring electrode also typically require spacing tolerances between adjacent ring electrodes. Such attachment methods often result in an acute angle at which the lead wire must extend to reach the ring electrode which can cause stress leading to detachment or breakage.

Flexible electronics, also known as flex circuits, is a technology for assembling electronic circuits by mounting electronic devices on flexible plastic substrates, such as polyimide, PEEK or transparent conductive polyester film. Additionally, flex circuits can be screen printed silver circuits on polyester. Flexible printed circuits (FPC) are made with a photolithographic technology. An alternative way of making flexible foil circuits or flexible flat cables (FFCs) is laminating very thin (0.07 mm) copper strips in between two layers of PET. These PET layers, typically 0.05 mm thick, are coated with an adhesive which is thermosetting, and will be activated during the lamination process. Single-sided flexible circuits have a single conductor layer made of either a metal or conductive (metal filled) polymer on a flexible dielectric film. Component termination features are accessible only from one side. Holes may be formed in the base film to allow component leads to pass through for interconnection, normally by soldering.

Accordingly, a need exists for an electrophysiological catheter with bipole microelectrode pairs that are very closely spaced to minimize detection of noise and/or far-field signals. There is also a need for a method of manufacture and assembly of such a catheter wherein very close spacing between electrodes can be achieved readily and consistently with improved precision and accuracy.

SUMMARY OF THE INVENTION

The present invention is directed to an electrophysiologic catheter with a distal electrode assembly carrying very closely-spaced bipole microelectrodes on a plurality of divergent spines that can flexibly spread over tissue surface area for simultaneously detecting signals at multiple locations with minimized detection of undesirable noise, including far-field signals.

In some embodiments, the catheter includes an elongated body and a distal electrode assembly having at least one spine with a flexible microelectrode panel. The spine has a free distal end, and the panel has a substrate conforming to an outer surface of the spine, at least one pair of microelectrodes, a trace for each microelectrode, and a soldering pad for each microelectrode, wherein each trace electrically couples a respective microelectrode and a respective soldering pad.

In some detailed embodiments, adjacent microelectrodes of a bipole pair are separated by a space gap distance of about 300 microns or less, including about 200 microns or less. In some detailed embodiments, the space gap distance ranges between about 50 and 100 microns. In some detailed embodiments, the space gap distance is about 50 microns.

In some detailed embodiments, each microelectrode has a width of about 300 microns, a width of about 200 microns, or a width of about 100 microns.

In some detailed embodiments, each microelectrode has an enlarged portion configured to cover a trace electrical connection.

In some detailed embodiments, each spine has a circular cross-section.

In some detailed embodiments, each spine has a rectangular cross-section.

In other embodiments, the catheter has an elongated body, and a distal electrode assembly having a plurality of divergent spines, and a flexible panel on at least one spine, wherein the panel has a substrate conforming to an outer surface of the spine, a pair of microelectrodes, and a trace electrically coupling a respective microelectrode and a respective soldering pad, and wherein the pair of microelectrodes are at least partially circumferentially wrapped around the spine, and microelectrodes of the pair are separated by a space gap distance ranging between about 50-200 microns.

In detailed embodiments, the spine has a planar surface configured to contact tissue surface, and the pair of microelectrodes are positioned on the planar surface.

In detailed embodiments, the entirety of the pair of microelectrodes is within the planar surface.

In detailed embodiments, each microelectrode has a width ranging between about 50-200 microns.

In additional embodiments, the catheter has an elongated body, and a distal electrode assembly having a plurality of spines, each spine having a free distal end and a preformed inward curvature toward a longitudinal axis of the assembly, and a flexible panel on at least one spine, the panel having a substrate conforming to an outer surface of the spine, a pair of microelectrodes, and a trace electrically coupling a respective microelectrode and a respective soldering pad, wherein the pair of microelectrodes are at least partially circumferentially wrapped around the spine, and microelectrodes of the pair are separated by a space gap distance ranging between about 50-300 microns, 50-200 microns, or 50-100 microns.

In some detailed embodiments, the flexible panel has a longitudinal portion, at least a distal lateral portion, and a proximal base portion, wherein the trace is positioned in the longitudinal portion, the pair of microelectrodes are positioned in the distal lateral portion and the soldering pad is positioned in the distal base portion.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

DETAILED DESCRIPTION OF THE INVENTION

Figure 1:
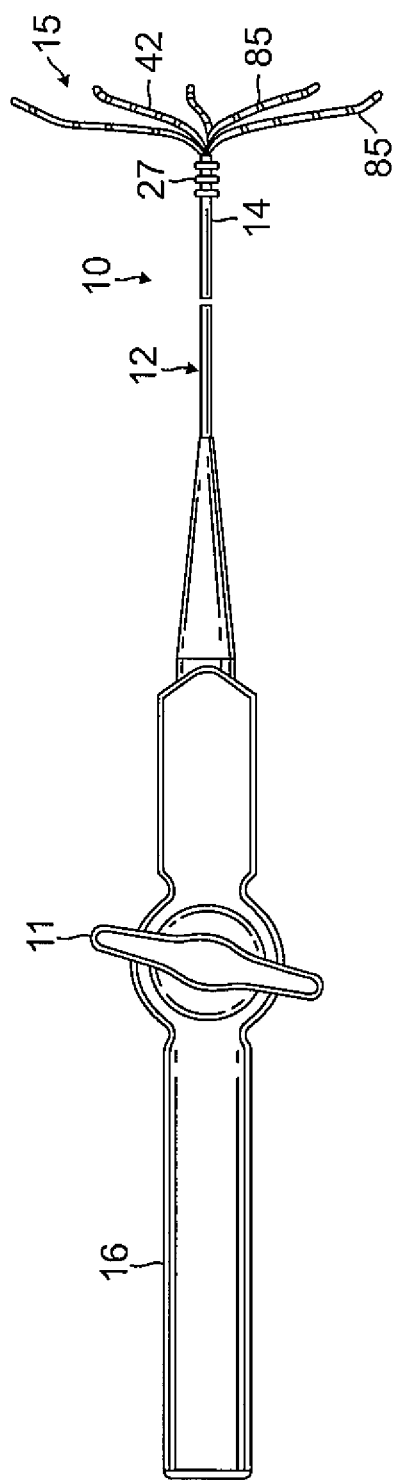
FIG. 1 is a side view of a catheter of the present invention, according to an embodiment.

Referring to FIG. 1, in some embodiment of present invention, a catheter 10 includes a catheter body 12, an intermediate deflection section 14, a distal electrode assembly 15, and a control handle 16 proximal of the catheter body 12. The distal electrode assembly 15 includes a plurality of spines 42, each spine carrying at least one pair of closely-spaced bipole microelectrodes 85, wherein the microelectrodes of a pair has a separation space gap distance therebetween of no greater than about 200 microns.

Figure 2:
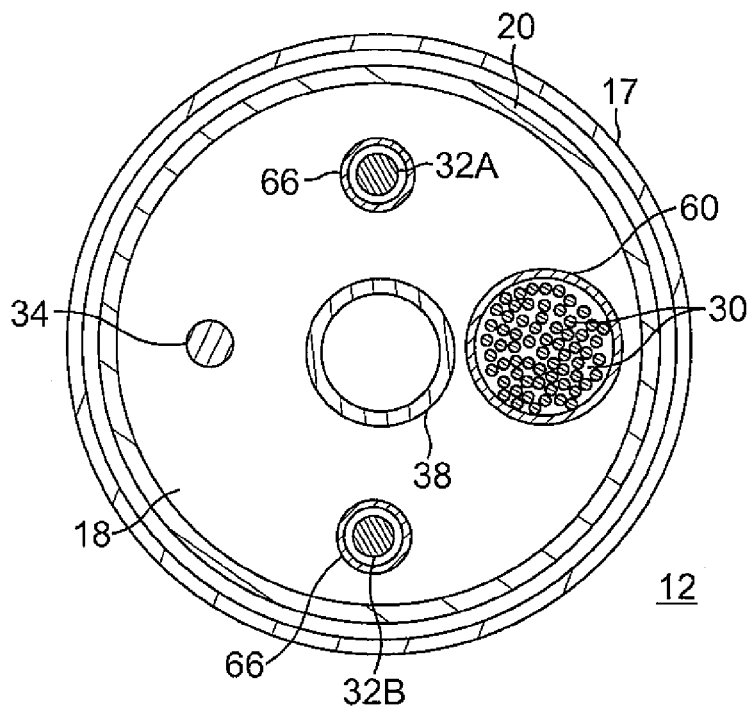
FIG. 2 is an end cross-sectional view of a catheter body of the catheter of FIG. 1, taken along line 2-2.

In some embodiments, the catheter body 12 comprises an elongated tubular construction, having a single, axial or central lumen 18, as shown in FIG. 2. The catheter body 12 is flexible, i.e., bendable, but substantially non-compressible along its length. The catheter body 12 can be of any suitable construction and made of any suitable material. A presently preferred construction comprises an outer wall 17 made of a polyurethane, or PEBAX. The outer wall 17 comprises an imbedded braided mesh of high-strength steel, stainless steel or the like to increase torsional stiffness of the catheter body 12 so that, when the control handle 16 is rotated, the deflection section 14 of the catheter 10 will rotate in a corresponding manner.

The outer diameter of the catheter body 12 is not critical, but is preferably no more than about 8 french, more preferably about 7 french. Likewise the thickness of the outer wall 17 is not critical, but is thin enough so that the central lumen 18 can accommodate components, including, for example, one or more puller wires, electrode lead wires, irrigation tubing, and any other wires and/or cables. The inner surface of the outer wall 17 is lined with a stiffening tube 20, which can be made of any suitable material, such as polyimide or nylon. The stiffening tube 20, along with the braided outer wall 17, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 17. Polyimide tubing is presently preferred for the stiffening tube 20 because it may be very thin walled while still providing very good stiffness. This maximizes the diameter of the central lumen 18 without sacrificing strength and stiffness. As would be recognized by one skilled in the art, the catheter body construction can be modified as desired. For example, the stiffening tube can be eliminated.

Figure 3:
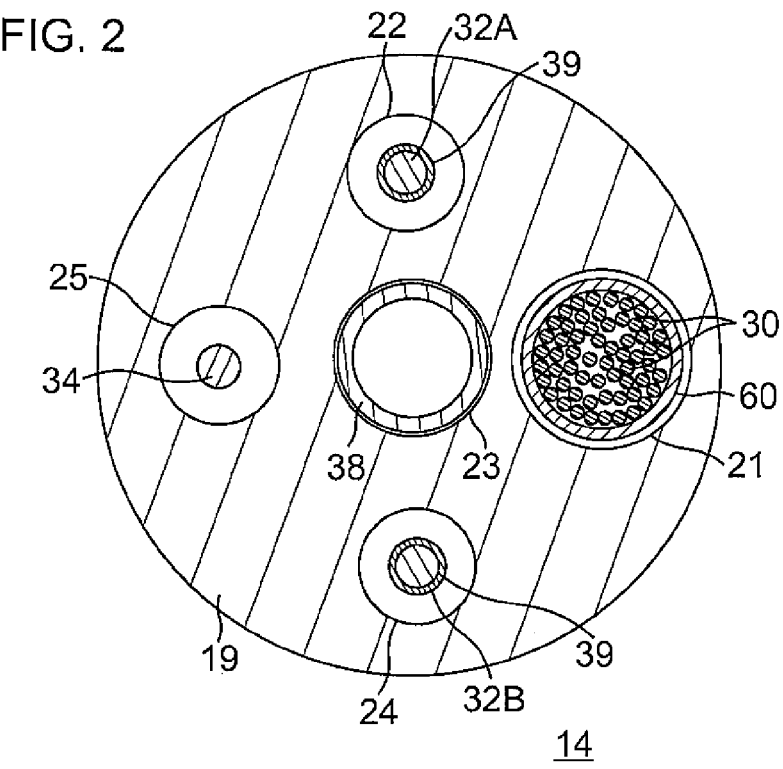
FIG. 3 is an end cross-sectional view of a deflection section of the catheter of FIG. 1, taken along line 3-3.

In some embodiments, the intermediate deflection section comprises a shorter section of tubing 19, which as shown in FIG. 3, has multiple lumens, for example, off-axis lumens 21, 22, 23 and 24 and on axis lumen 25. In some embodiments, the tubing 19 is made of a suitable non-toxic material more flexible than the catheter body 12. A suitable material for the tubing 19 is braided polyurethane, i.e., polyurethane with an embedded mesh of braided high-strength steel, stainless steel or the like. The outer diameter of the deflection section 14 is similar to that of the catheter body 12. The size of the lumens is not critical and can vary depending on the specific application.

Various components extend through the catheter 10. In some embodiments, the components include lead wires 30 the distal electrode assembly 15, one or more puller wires 32A and 32B for deflecting the deflection section 14, a cable 34 for an electromagnetic position sensor 36 housed at or near a distal end of the deflection section 14, and a guidewire tubing 38. These components pass through the central lumen 18 of the catheter body 12, as shown in FIG. 2.

In the deflection section 14, different components pass through different lumens of the tubing 19 as shown in FIG. 3, In some embodiments, the lead wires 30 pass through first lumen 21, the first puller wire 32A passes through second lumen 32, the guidewire tubing 38 passes through third lumen 23, the cable 34 passes through fourth lumen 24, and the second puller 34B passes through fifth lumen 25. The second and fourth lumens 22 and 24 are diametrically opposite of each other to provide bi-directional deflection of the intermediate deflection section 14.

Figure 4:
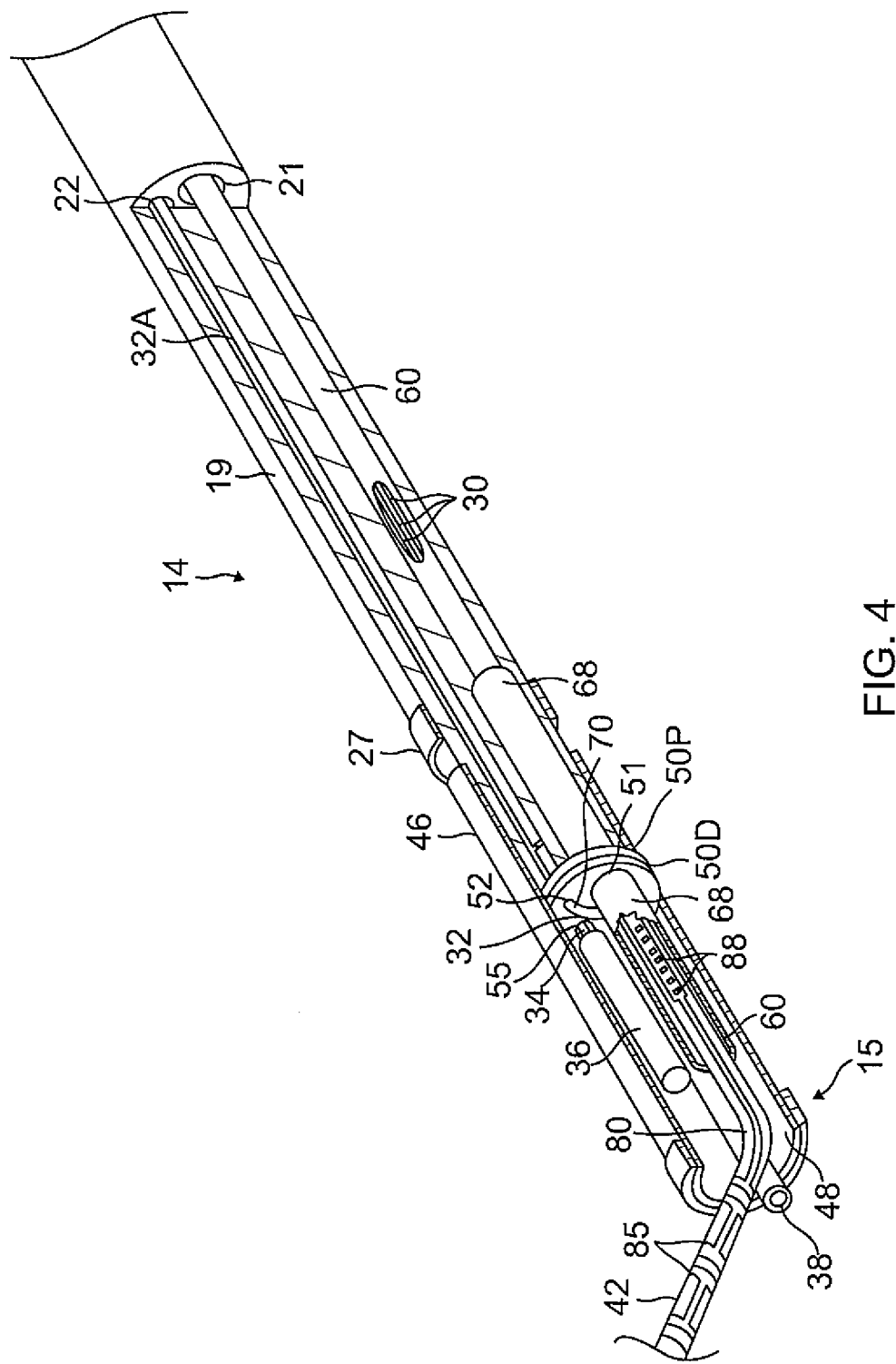
FIG. 4 is a perspective view of a junction between the deflection section and a distal electrode assembly of a catheter of the present invention, according to an embodiment, with parts broken away.

Distal of the deflection section 14 is the distal electrode assembly 15 which includes a mounting stem 46 in the form of a short tubing mounted on a distal end of the tubing 19 of the intermediate deflection section 14. (In that regard, it is understood that where the catheter 10 is without a deflection section 14, the mounting stem 46 is mounted on a distal end of the catheter body 12.) The stem 46 has a central lumen 48 to house various components. The intermediate section 14 and stem 46 are attached by glue or the like. The stem 46 may be constructed of any suitable material, including nitinol. As shown in FIG. 4, the stem 46 houses various components, including the electromagnetic position sensor 36, and a distal anchor for the puller wires 32A and 32B.

In the disclosed embodiment, the distal anchor includes one or more washers, for example, a distal washer 50D and a proximal washer 50P, each of which has a plurality of through-holes that allow passage of components between the deflection section 14 and the stem 46 while maintaining axial alignment of these components relative to a longitudinal axis 40 of the catheter 10. The through-holes include holes 52 and 54 that are axially aligned with the second and fourth lumens 22 and 24 of the tubing 19, respectively, to receive a distal end of puller wires 32A and 32B, respectively. It is understood that the puller wires may form a single tensile member with a distal U-bend section that passes through the holes 52 and 54. With tension on the washers 50D and 50P exerted by the U-bend section of the puller wires, the washers firmly and fixedly abut against the distal end of the tubing 19 of the deflection section 14 to distally anchor the U-bend section.

Each washer includes through-hole 51 which is axially aligned with the first lumen 21 and allows passage of the lead wires 30 from the deflection section 14 and into the lumen 48 of the stem 46. Each washer also includes through-hole 55 which is axially aligned with the fifth lumen 25 of the tubing 19 and allows passage of the sensor cable 34 from the deflection section 14 into lumen 48 of the stem 46 where the electromagnetic position sensor 36 is housed. Each washer further includes on-axis through-hole 53 which is axially aligned with the third lumen 23 and allows passage of the guidewire tubing 38 from the deflection section 14 and into the lumen 48 of the stem 45. Marker bands or ring electrodes 27 may be carried on the outer surface of the catheter at or near the near the distal end of the intermediate deflection section 14, as known in the art.

As shown in FIG. 4, extending from the distal end of the stem 46 are elongated spines 42 of the distal electrode assembly 15. Each spine has a support member 43, a non-conductive covering 44 that extends along the each spine 42. Each spine has a proximal portion that extends proximally into the lumen 48 of the stem 46. The non-conductive coverings 44 of the spines may also extend proximally into the lumen 48. Each spine 42 may be arranged uniformly about the distal opening of the stem 46 in equi-radial distance from adjacent spines 42. For example, with five spines, each spine may be spaced apart at about 72 degrees from adjacent spines. Suitable adhesive, e.g., polyurethane, may be used to pot and anchor the proximal ends of the spines 42 and their nonconductive coverings 44. The suitable adhesive seals the distal end of the stem 46, which is formed to leave open the distal end of the guidewire tubing 38.

Each spine support member 43 is made of a material having shape-memory, i.e., that can be temporarily straightened or bent out of its original shape upon exertion of a force and is capable of substantially returning to its original shape in the absence or removal of the force. One suitable material for the support member is a nickel/titanium alloy. Such alloys typically comprise about 55% nickel and 45% titanium, but may comprise from about 54% to about 57% nickel with the balance being titanium. A nickel/titanium alloy is nitinol, which has excellent shape memory, together with ductility, strength, corrosion resistance, electrical resistivity and temperature stability. The non-conductive covering 44 can be made of any suitable material, and is preferably made of a biocompatible plastic such as polyurethane or PEBAX.

Lead wires 30 for microelectrodes 85 carried on the spines 42 extend through the catheter body 12 and the deflection section 14 protected by a nonconductive sheath 60. Toward the distal electrode assembly 15, the lead wires 30 extend through a polytube 68, as shown in FIG. 4. The lead wires 30 diverge at the distal end of the polytube 68, and extend toward their respective spine 42.

Figure 5:
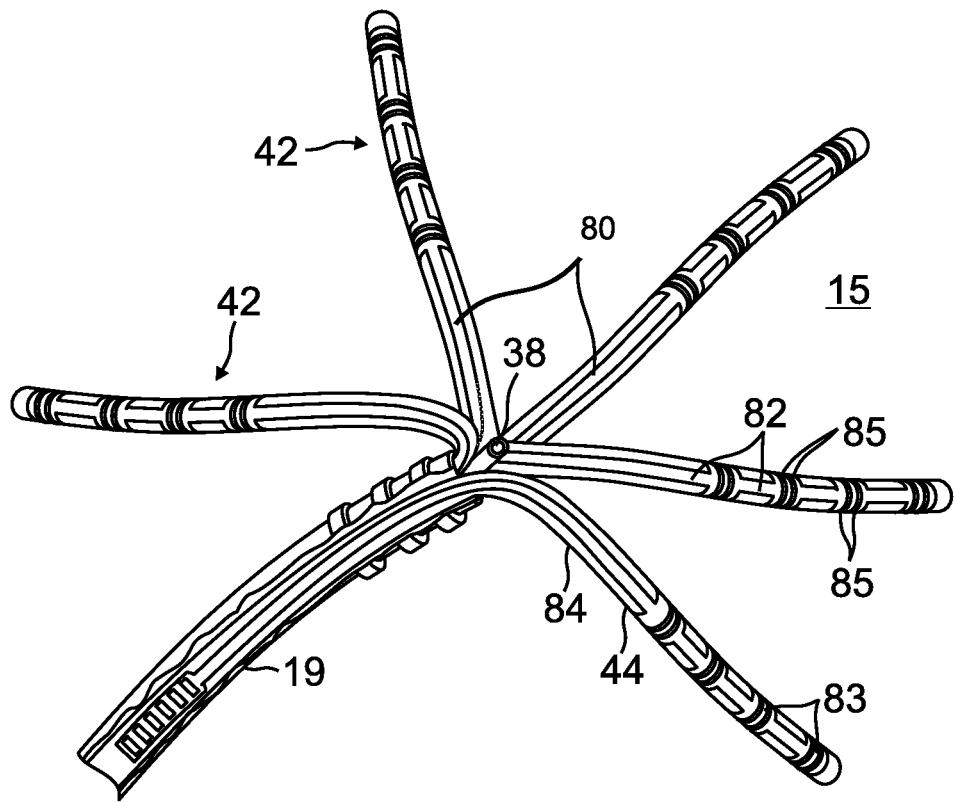
FIG. 5 is a perspective view of a distal electrode assembly of the present invention, according to an embodiment.
Figure 6:
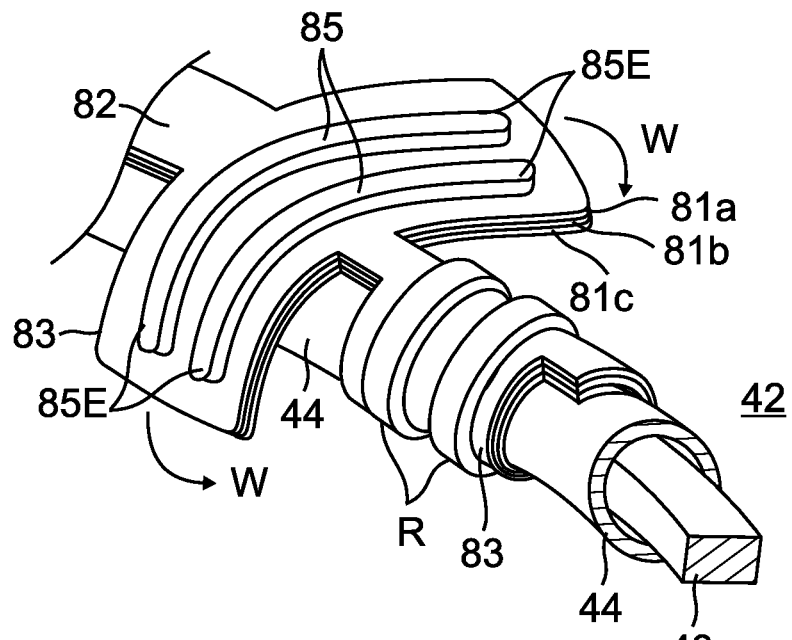
FIG. 6 is a detailed view of a flexible microelectrode panel and a spine during assembly, according to an embodiment.

As shown in FIG. 5 and FIG. 6, each spine 42 includes a flexible microelectrode member in the form of a panel 80 that is affixed to the outer surface of spine 42, conforming to the shape of the spine 42. The flexible electrode panel 80, as better shown in FIG. 7, includes a biocompatible flexible plastic substrate 81 constructed of a suitable material, for example, polyimide or PEEK, at least one pair of close-spaced microelectrodes 85, separated therebetween by a gap space S.

Figure 7:
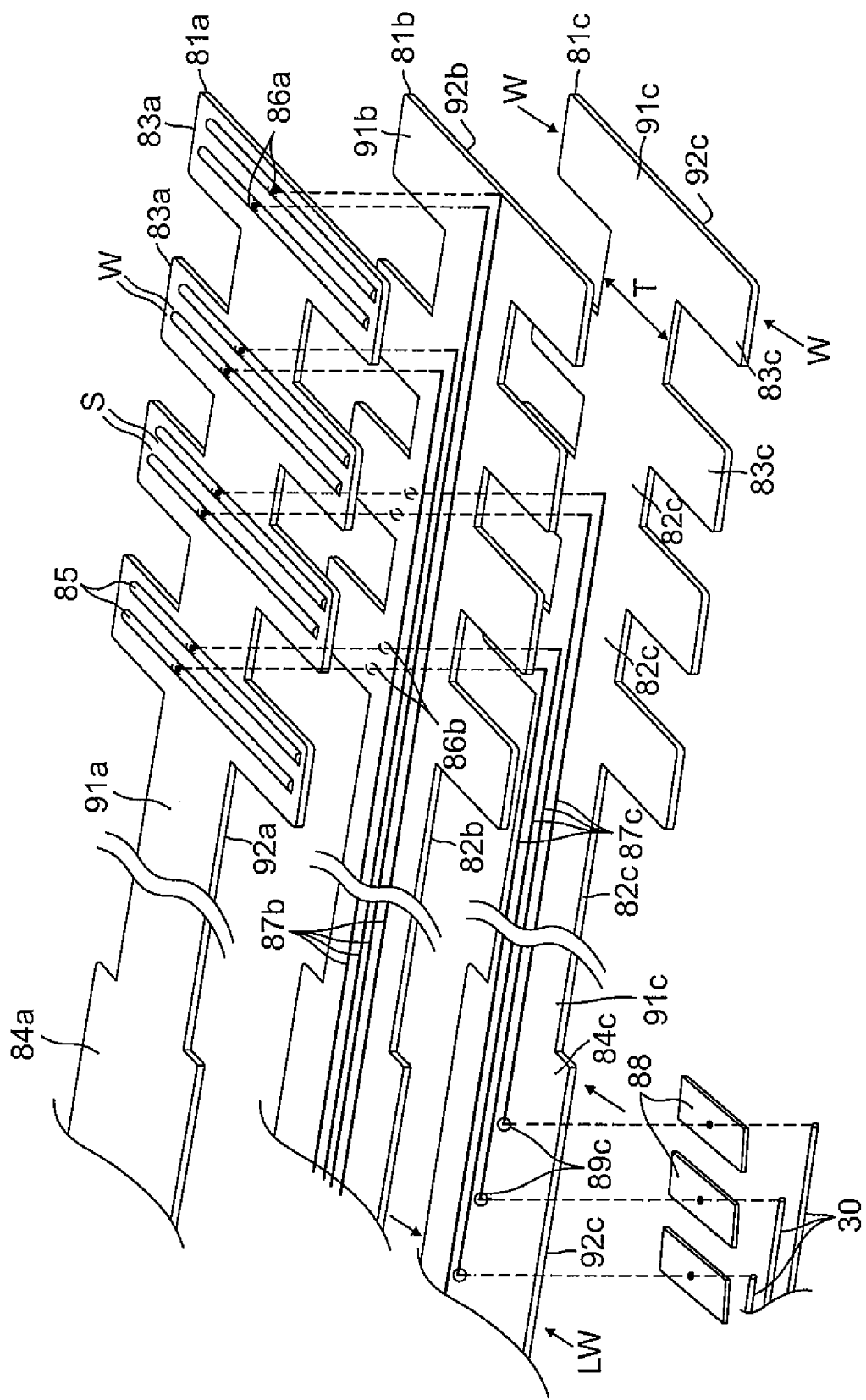
FIG. 7 is a partial exploded perspective view of a flexible microelectrode panel, according to an embodiment.

In some embodiments, the substrate 81 is generally elongated with a longitudinal (thinner "T") portion 82, at least one distal lateral (wider "W") portion 83 traversing the longitudinal portion 82 at a generally perpendicular angle, and a proximal (less wide "LW") base portion 84 having a slightly greater lateral dimension than the longitudinal portion 82 (T, W and LW shown in FIG. 7). The longitudinal portion 82 is configured to extend along the length of a spine 42 and the lateral portion 83 is configured to wrap circumferentially around a distal portion of the spine 42. The base portion 84 is positioned on a proximal end portion of the spine 42 and is thus protected within the lumen 48 of the mounting stem 46. On the base portion 84 are soldering patches 88, one for each lead wire 30 whose distal end is soldered to a respective soldering patch 88. The soldering patches 88 are therefore protected and insulated within the lumen 48 of the mounting stem 46. It is understood that only one spine member 42 is shown in FIG. 4 for purposes of clarity, and that the polytube 68 may be sized appropriately to receive the proximal ends of all spine members 42 extending from the tubing 19, where, in some embodiments of the present invention, the plurality of spine members 42 may range between about two and eight.

In other embodiment, the most proximal longitudinal portion 82 may be significantly elongated such that the base portion 84 is located further proximally in the deflection section 14, the catheter body 12, or even in the control handle 16, as appropriate or desired.

On an outer surface of each lateral portion 83, a respective pair of thin, elongated microelectrodes 85 (microelectrode strips) are affixed or otherwise provided in alignment with the lateral portion 83 so that each microelectrode generally forms a ring microelectrode R (FIG. 6) when the lateral portion 83 is wrapped circumferentially around the spine 42. It is understood that the longitudinal portion 82 may be as wide as the lateral portion 83 although the amount of surface area coverage and/or thickness of the substrate affects the flexibility of the spine 42.

In some embodiments, the space gap distance S separating each microelectrode of a pair ranges between about 50 and 300 microns. In some embodiments, the space gap distance ranges between about 100-200 microns. In some embodiments, the space gap distance is about 50 microns. Moreover, in some embodiments, each microelectrode itself may have a width W ranging between about 50-100 microns. At least one pair of closely-spaced bipole microelectrodes 85 are provided on each spine 42. In the illustrated embodiment, each spine carries four pairs of bipole pairs for a total of eight microelectrodes.

In some embodiments, a panel 80 has a length of about 8.0 cm, wherein the longitudinal portion 82 has a length of about 5.0 cm and a width no greater than about 1.0 mm, and the base portion 84 has a length of about 3.0 cm and a width of about 1.2 mm. Each pair of microelectrodes is spaced apart from an adjacent pair of microelectrodes by a distance of about 5.0 mm, with each microelectrode having a width of about 50 microns, and a length of about 2.56 mm.

In some embodiments, the substrate 81 comprises multiple layers, for example, first or outer layer 81a, second or middle layer 81b, and third or inner layer 81c, each having a first surface 91 and a second surface 92. It is understood that the letters "a", "b" and "c" designate corresponding features in the layers 81a, 81b and 81c of the substrate 81. The microelectrodes 85 are applied to or otherwise deposited on the first surface 91a of the outer layer 81a, to overlie through-holes 86a which are formed in the layer 81a to provide connection access for electrical traces 87b that extend along the first surface 91b of the longitudinal portion 82b of the second layer 81b between corresponding microelectrodes 85 and soldering pads 88 carried on the second surface 92c of the base portion 84c of the third layer 81c. Additional traces 87c run along the first surface 91c of the third layer 81c. Through-holes 86b, 89b (not shown) and 89c are formed in the layers 81b and 81c to provide connection access for the electrical traces 87b and 87c to more proximal microelectrodes 85, and more proximal soldering pads (not shown in FIG. 7). It is understood that the plurality of layers 81 depends on the amount of surface and space available thereon to accommodate the plurality of traces 87 connecting the microelectrodes 85 and the soldering pads 88. It is also understood that with increasing layers flexibility of the spines can be reduced. Thus, the plurality of layers to accommodate the plurality of microelectrodes is balanced against the flexibility of the spines which enable conformity to tissue surface but decreases with increasing substrate thickness. In the illustrated embodiment of FIG. 7, the substrate 81 has three layers with each layer 81 carrying four traces. It is understood that there is one corresponding trace 87 and one corresponding soldering pad 88 for each microelectrode 85. Each lead wire 30 is soldered to a corresponding soldering pad. In that regard, it is also understood that the traces may be arranged differently, in different patterns and/or on different layers, as needed or appropriate.

As shown in FIG. 5 and FIG. 6, the substrate 81 is affixed to the nonconductive covering 44 of the spine 42 with the longitudinal portion 82 extending longitudinally along the spine 42 and the lateral portions 83 wrapped circumferentially around the spine 42. In that regard, the lateral dimension or width W of the lateral portions 83, and more significantly of the microelectrodes 85, is comparable to the circumference of the spine 42 such that opposing ends 85E of the microelectrodes can reach each other or at least come in close contact to generally form and function as ring microelectrodes R carried on the spine 42. In the illustrated embodiment of FIG. 5, the substrate 81 is affixed to the forward-facing or distal side of the spine that is adapted to contact tissue, although it is understood that the placement side of the substrate is less critical where the microelectrodes are long enough to wrap around the spine. In another embodiment discussed further below, placement side is more critical where the lateral dimension W is adjusted and decreased as desired or appropriate for lesser circumferential reach around the spine 42.

Figure 8:
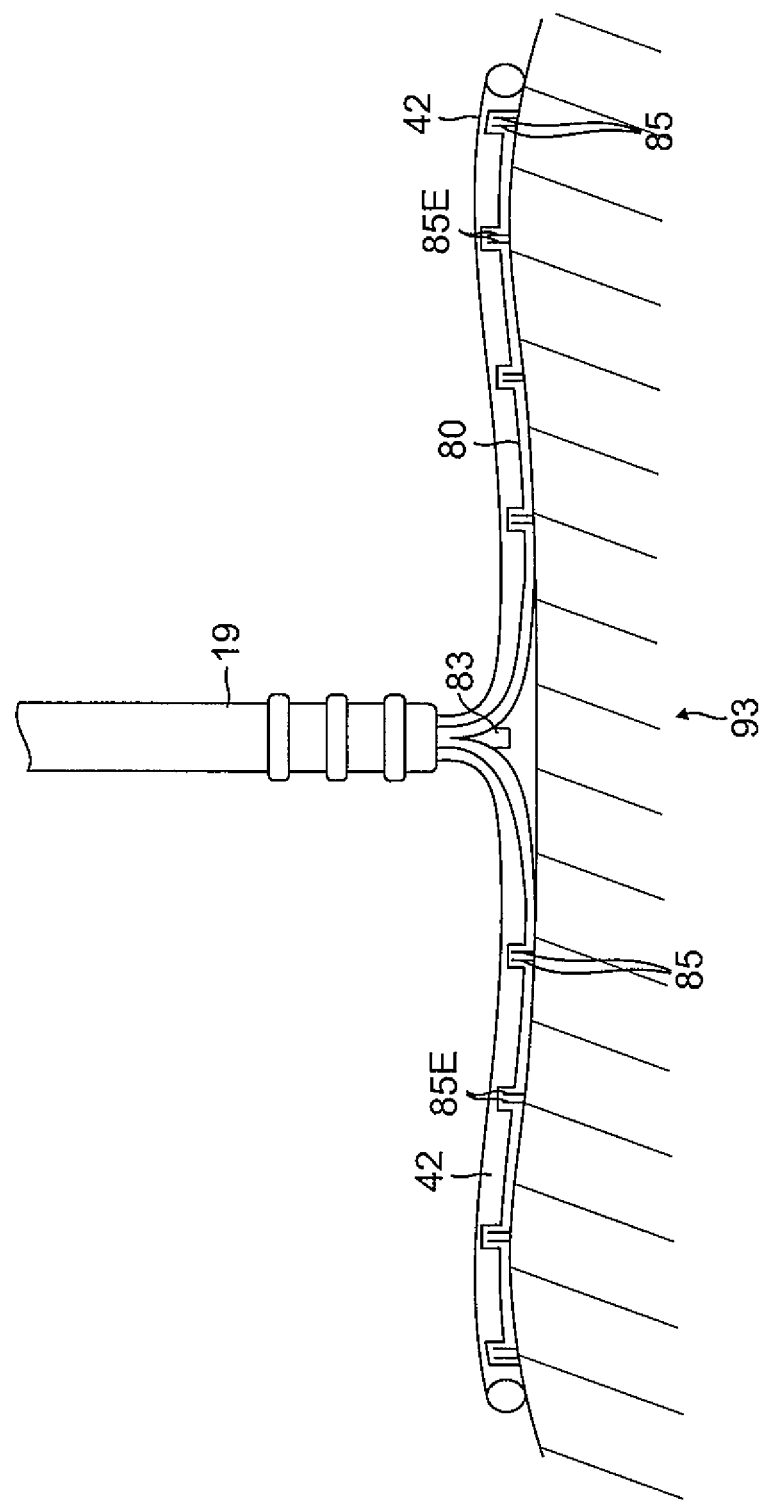
FIG. 8 is a side view of a distal electrode assembly of FIG. 5 in contact with tissue surface.

As shown in FIG. 5, each spine 42 is preformed with a slight inward curvature such that the distal electrode assembly 15 has a generally slightly concave configuration resembling an open umbrella. This preformed configuration enables each spine 42 to engage tissue surface 93 generally along its entire length when catheter is advanced distally against tissue surface, as shown in FIG. 8. Without the preformed configuration, the distal electrode assembly 15 may tend to flip outwardly (much like an umbrella flipping inside out under strong wind) and lose tissue contact as the catheter is pushed distally against tissue surface.

Figure 9:
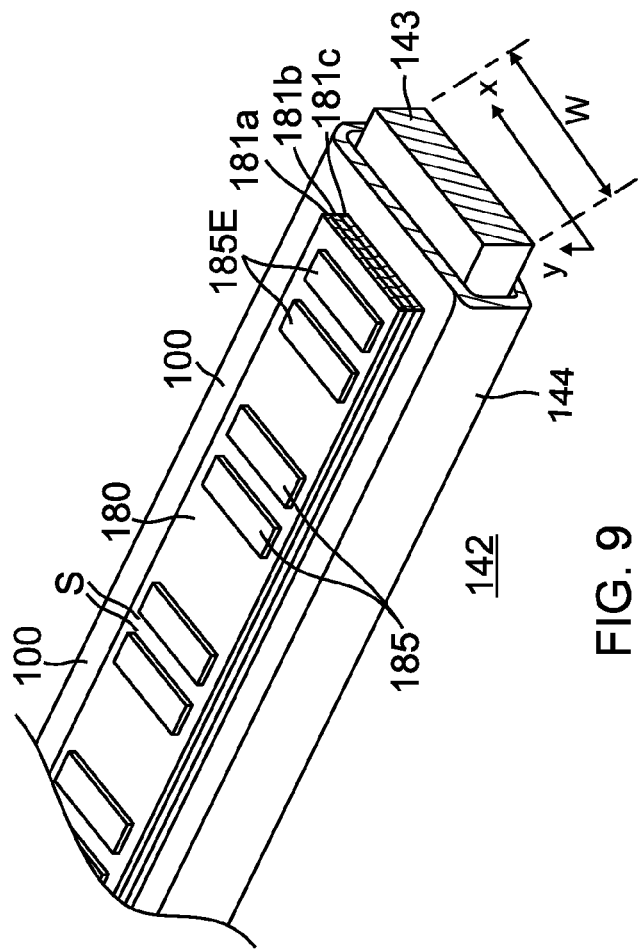
FIG. 9 is a detailed view of a spine with a flexible microelectrode panel, according to another embodiment.
Figure 11:
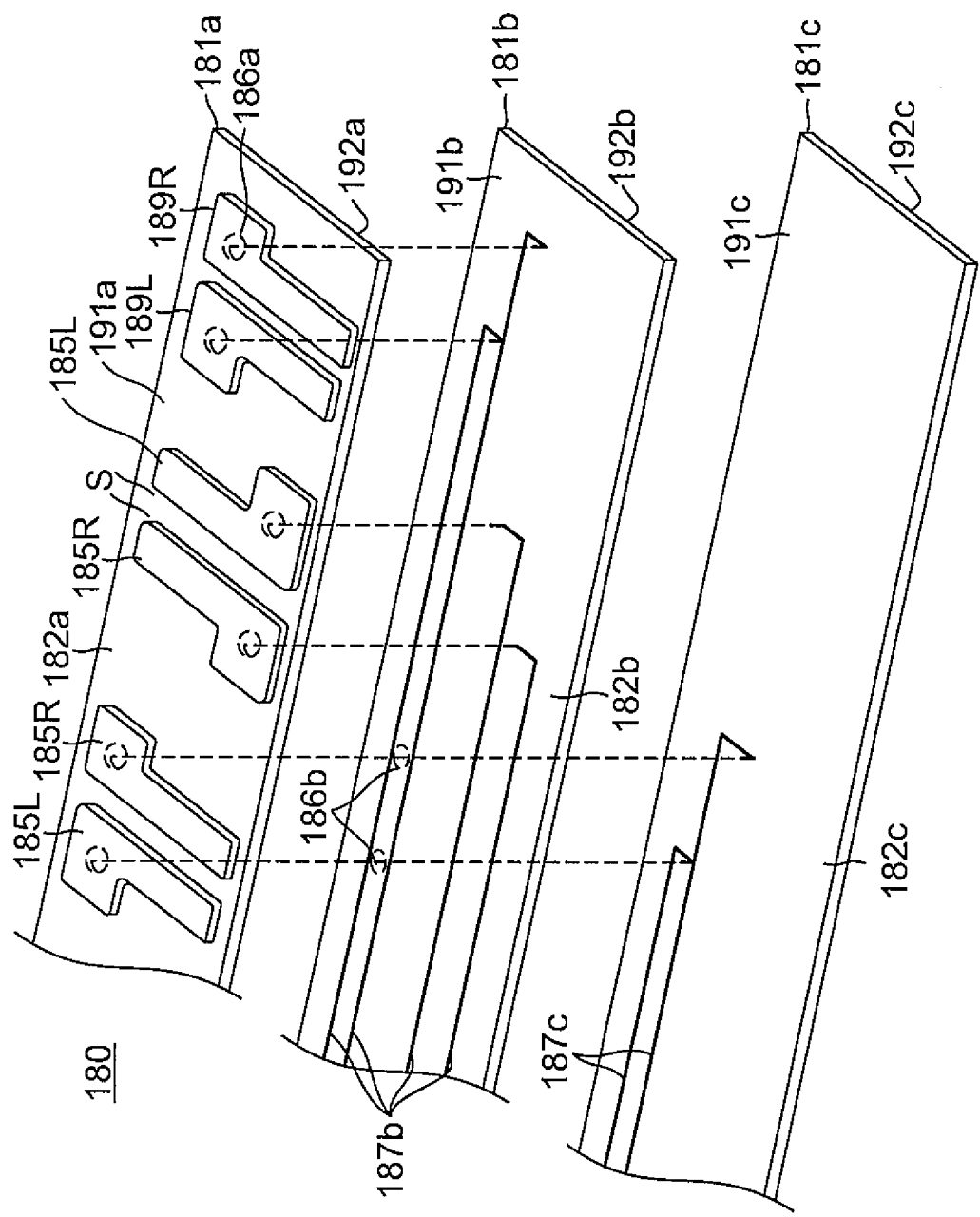
FIG. 11 is a partial exploded perspective view of a distal electrode assembly with spines in accordance with the embodiment of FIG. 9.

As FIG. 8 illustrates, ends 85E of microelectrodes may not be in contact with tissue surface which exposes the microelectrodes to detecting undesirable noise, for example, far-field signals. Accordingly, FIG. 9 and FIG. 11 illustrate distal electrode assembly 117 of an alternate embodiment which provides a greater planar surface for tissue contact that minimizes exposure of the microelectrodes to noise and far field signals. It is understood that similar components between the distal electrode assembly 17 and distal electrode assembly 117 are designated by similar reference numbers for ease of discussion herein.

Figure 10:
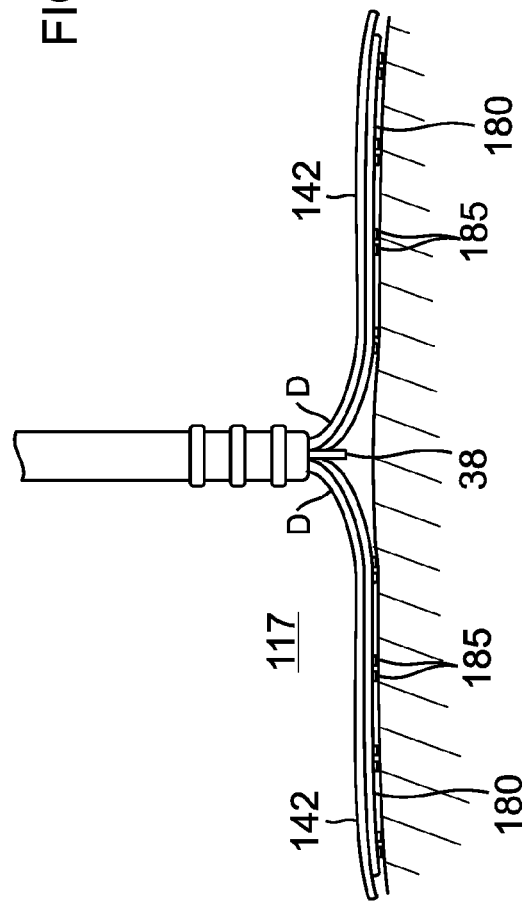
FIG. 10 is a side view of a distal electrode assembly in contact with tissue surface, according to another embodiment.

Whereas the spine 42 of FIG. 6 has a more circular cross-section, spine 142 of FIG. 9 has a more rectangular cross section which provides the greater planar surface 100 on which flexible microelectrode member in the form of panel 180 can be selectively applied or affixed. Advantageously, the entirety of the microelectrodes 185 (including their ends 180E) is confined to the surface area of the planar surface 100 and therefore generally the entirety of microelectrodes 185 is in contact with tissue when the planar surface 100 is in contact with tissue 193, as shown in FIG. 10.

Support member 143 has a rectangular cross-section which is adopted by heat-shrink nonconductive covering 144 to provide the greater planar surface 100. In some embodiments, the panel 180 as shown in FIG. 11 has substrate 181, microelectrodes 185, traces 187 and soldering pads 188 (not shown) having similar construction as their counterparts described above for panel 80. The substrate 181 comprises multiple layers, for example, first or outer layer 181a, second or middle layer 181b, and third or inner layer 181c, each having a first surface 191 and a second surface 192. However, as one difference, the substrate 181 is devoid of lateral portions, with a longitudinal portion 182 having a lateral dimension W that is comparable or at least no greater than the lateral dimension of the planar surface 100 so that the substrate 181 remains confined on the planar surface 100. The microelectrodes 185 are elongated and thin. To achieve a minimum space gap S between adjacent microelectrodes 185 of a pair while accommodating through-holes 186, microelectrodes 185 have enlarged portions or ends 189, as shown in FIG. 11, that are sized larger than the through-holes 186 to span and overlie the through-holes 186 so that traces 187b and 187e can be connected to the microelectrodes 185. In one embodiment, the microelectrode has a width of about 50 microns and the enlarged portion 189 has a width of about 100 microns.

Figure 12A:
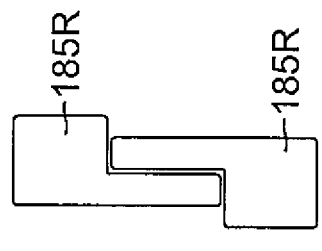
FIG. 12A, FIGS. 12B, 12C and 12D are top plan views of arrangements of microelectrodes according to different embodiments.
Figure 12B:
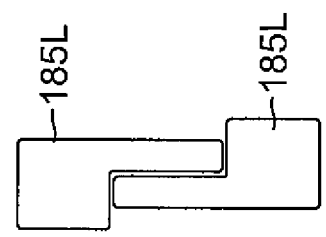
Figure 12C:
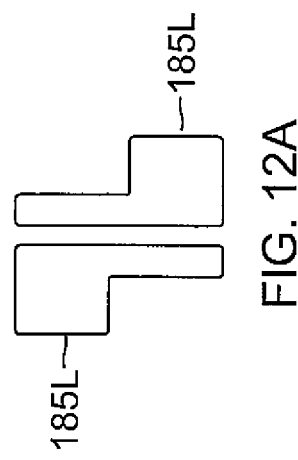
Figure 12D:
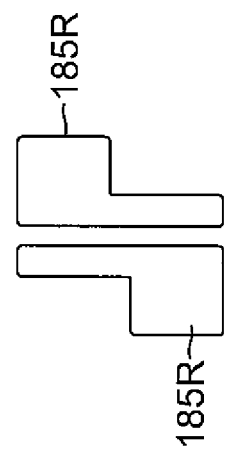

The enlarged portion or end 189 of a microelectrode may extend to the right (forming a "right-handed microelectrode" 185R) or to the left (forming a "left-handed microelectrode" 185L), as shown in FIG. 11. A pair may comprise a right-handed microelectrode 185R and a left handed microelectrode 185L, as shown in FIG. 11, or two right-handed microelectrodes 185R-185R, as shown in FIG. 12B and FIG. 12C, or two left-handed microelectrodes 185L-185L, as shown in FIG. 12A and FIG. 12D. The microelectrodes of a pair may be arranged in any formation, including, for example, a mirrored pairs (FIG. 11), as upside down pairs (FIG. 12A, FIG. 12B, FIG. 12C, and FIG. 12D), as side-by-side pairs (FIG. 11, FIG. 12A and FIG. 12B), or as stacked pairs (FIG. 12C and FIG. 12D). In any case, the enlarged portions ends are turned outwardly away from each other so that the space gap distance as defined between adjacent linear edges can be minimized.

As described above in relation to FIG. 7, the microelectrodes 185 of FIG. 9 and FIG. 11 are similarly affixed to the front surface 191a of the longitudinal portion 182a of the first layer 181a, and soldering pads 188 are affixed to the second surface 192c of the base portion 184c of the third layer 181c. Traces 187b and 187c run along the second and third layers 181b and 181c, respectively. Through-holes 186a, 189b and 189c are formed in the layers 181a, 181b and 181c, respectively, to provide the traces with connection access to the microelectrodes 185 and the soldering pads 188 (not shown). Again, it is understood that the plurality of layers 181 depends on the amount of surface and space available thereon to accommodate the plurality of traces 187 connecting the microelectrodes 185 and the soldering pads 188, which accommodation is balanced against the desired flexibility of the spine 142 with the understanding that increasing thickness of the substrate can decrease the flexibility of the spine 42. In the illustrated embodiments of FIG. 9 and FIG. 11, each layer 181 accommodates four traces for a total of eight traces servicing eight microelectrodes and eight soldering pads.

With each spine 142 preformed with a slight inward curvature such that the distal electrode assembly 115 has a generally slightly concave configuration resembling an open umbrella, the planar surface 100 and the microelectrodes 185 thereon can fully engage and make contact with tissue surface so as to minimize exposure of the microelectrodes to noise and far-field signals without flipping inside out, as shown in FIG. 8. The substrate 181 is selectively affixed to the forward-facing or distal side of the spine 142 where the planar surface 100 is adapted to contact tissue surface with minimal exposure of the microelectrodes 185 to noise and far-field signals.

Distal electrode assembly 115 having spines 142 with a rectangular cross-section wherein the X dimension along the planar surface 100 is greater than the Y dimension perpendicularly thereto, as shown in FIG. 9, is also particularly adapted for minimizing kinking and stress to the spines at their area of greatest flexion or divergence D (see FIG. 10) located slightly distal of the distal end of stem 146.

It is understood that as the need or desire arises, any given spine may carry one or more flexible electrode panel of the same or different embodiments, as described above.

Figure 13:
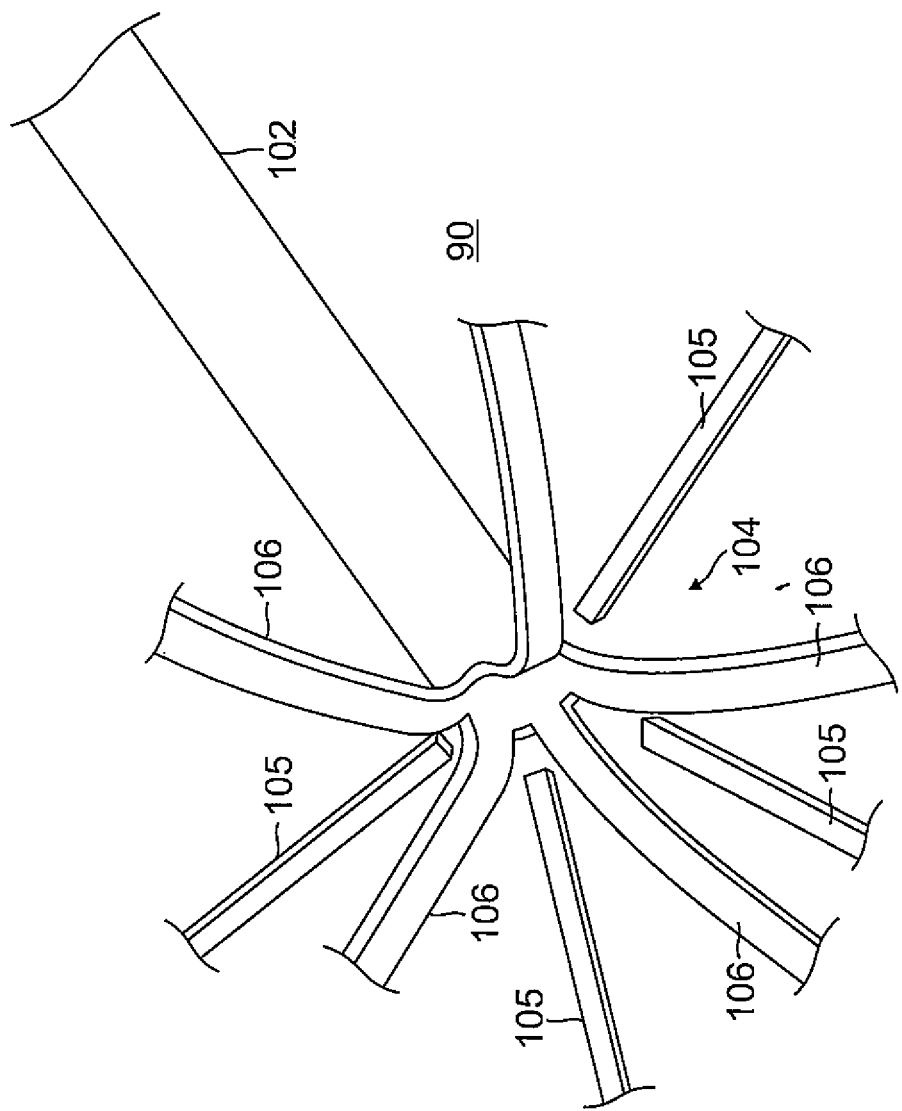
FIG. 13 is a detailed view of a spine support member in accordance with one embodiment.

In some embodiments, the spine support members 43/143 are formed from a single elongated hollow cylinder or tube 90, as shown in FIG. 13, with an intact proximal cylindrical portion 102 (which may form the stem 46/146 of the distal electrode assembly), and a distal portion 104 with formed elongated extensions or fingers 106 that function as the plurality of support members 43, separated by space gaps therebetween that are formed by longitudinal cuts in the sidewall of the cylinder 90, or by removal, e.g., laser cutting, of elongated longitudinal strips 105 from the sidewall of cylinder 90. Each finger 106 is shaped to diverge or splay outward at or near its proximal end and to have a slight inward curvature, as shown in FIG. 5.

In the depicted embodiment, the lead wires 30 extending through the central lumen 18 of the catheter body 12 and the first lumen 21 in the deflection section 14 may be enclosed within a protective sheath 60 to prevent contact with other components in the catheter. The protective sheath 60 may be made of any suitable material, preferably polyimide. As would be recognized by one skilled in the art, the protective sheath can be eliminated if desired.

The microelectrodes 85 can be made of any suitable solid conductive material, such as platinum or gold, preferably a combination of platinum and iridium. The closely-spaced microelectrode pairs allow for more accurate detection of near field pulmonary vein potential versus far field atrial signals, which is very useful when trying to treat atrial fibrillation. Specifically, the near field pulmonary vein potentials are very small signals whereas the atria, located very close to the pulmonary vein, provides much larger signals. Accordingly, even when the mapping array is placed in the region of a pulmonary vein, it can be difficult for the physician to determine whether the signal is a small, close potential (from the pulmonary vein) or a larger, farther potential (from the atria). Closely-spaced bipole microelectrodes permit the physician to more accurately determine whether he/she is looking at a close signal or a far signal. Accordingly, by having closely-spaced microelectrodes, one is able to better target the locations of myocardial tissue that have pulmonary vein potentials and therefore allows the clinician to deliver therapy to the specific tissue. Moreover, the closely-spaced microelectrodes allow the physician to better determine the anatomical location of the ostium/ostia by the electrical signal.

As described above, the electromagnetic position sensor 36 is housed in the lumen 48 of the stem 46, as shown in FIG. 4. The sensor cable 34 extends from a proximal end of the position sensor, via through-hole 55 (not shown) of the washers 50D and 50P, the fifth lumen 25 of the tubing 19 of the deflection section 14 (see FIG. 3), and the central lumen 18 of the catheter body 12 (see FIG. 2). The cable 34 is attached to a PC board in the control handle 16, as known in the art. In some embodiments, one or more distal electromagnetic position sensors may be housed in the distal electrode assembly, for example, in one or more distal portions of the spines 42.

As shown in FIG. 3 and FIG. 4, the puller wires 32A and 32B (whether as two separate tensile members or parts of a single tensile member) are provided for bi-directional deflection of the intermediate section 14. The puller wires are actuated by mechanisms in the control handle 16 that are responsive to a thumb control knob or a deflection control knob 11 (see FIG. 1). Suitable control handles are disclosed in U.S. Pat. Nos. 6,123,699; 6,171,277; 6,183,435; 6,183,463; 6,198,974; 6,210,407 and 6,267,746, the entire disclosures of which are incorporated herein by reference. The puller wires 32A and 32B extend through the central lumen 18 of the catheter body 12 (see FIG. 2) and through the second and fourth lumens 22 and 24, respectively, of the tubing 19 of the deflection section 14 (see FIG. 3). They extend through holes 52 and 54, respectively of the washers 50D and 50P (see FIG. 4). Where the puller wires are part of a single tensile member, the single tensile member has a U-bend at the distal face of the distal washer 50D which anchors the distal ends of the puller wires. In that regard, the U-bend extends through a short protective tubing 70. Alternatively, where the puller wires are separate tensile members, their distal ends may be anchored via T-bars, as known in the art and described in, for example, U.S. Pat. No. 8,603,069, the entire content of which is incorporated herein by reference. In any case, the puller wires may be made of any suitable metal, such as stainless steel or Nitinol, and each is preferably coated with TEFLON or the like. The coating imparts lubricity to the puller wires. The puller wires preferably have a diameter ranging from about 0.006 to about 0.010 inch.

A compression coil 66 is situated within the central lumen 18 of the catheter body 12 in surrounding relation to each puller wire 32A and 32B, as shown in FIG. 3. Each compression coil 66 extends from the proximal end of the catheter body 12 to the proximal end of the intermediate section 14. The compression coils 66 are made of any suitable metal, preferably stainless steel. Each compression coil 66 is tightly wound on itself to provide flexibility, i.e., bending, but to resist compression. The inner diameter of the compression coil 66 is preferably slightly larger than the diameter of its puller wire. The TEFLON coating on each puller wire allows it to slide freely within its compression coil.

The compression coil 66 is anchored at its proximal end to the outer wall 17 of the catheter body 12 by a proximal glue joint (not shown) and at its distal end to the intermediate section 14 by a distal glue joint (not shown). Both glue joints may comprise polyurethane glue or the like. The glue may be applied by means of a syringe or the like through a hole made the sidewalls of the catheter body 12 and the tubing 19. Such a hole may be formed, for example, by a needle or the like that punctures the sidewalls which are heated sufficiently to form a permanent hole. The glue is then introduced through the hole to the outer surface of the compression coil 66 and wicks around the outer circumference to form a glue joint about the entire circumference of the compression coil.

Within the second and fourth lumens 22 and 24 of the intermediate section 14, each puller wire 32A and 32B extends through a plastic, preferably TEFLON, puller wire sheath 39 (FIG. 3), which prevents the puller wires from cutting into the sidewall of the tubing 19 of the deflection section 14 when the deflection section 14 is deflected.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. It is understood that a feature of the present invention is applicable to multiplying linear motion of a puller wire, contraction wire, or any other object requiring insertion, removal, or tensioning within a medical device, including the disclosed electrophysiology catheter. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. An electrophysiological catheter comprising:
   an elongated body;
   a distal electrode assembly comprising:
      a plurality of spines, each of the spines having a free distal end and a proximal end extending from a distal end of the elongated body; and
      a flexible panel on at least one of the spines, the flexible panel having a substrate conforming to a surface of its respective spine, at least one pair of microelectrodes, a trace for each of the microelectrodes, and a soldering pad for each of the microelectrodes, wherein each trace electrically couples a respective one of the microelectrodes and a respective one of the soldering pads.

2. The catheter of claim 1, wherein the microelectrodes of the at least one pair of microelectrodes are separated by a space gap distance ranging between about 50-300 microns.

3. The catheter of claim 1, wherein each microelectrode of the at least one pair of microelectrodes has a width ranging between about 50-300 microns.

4. The catheter of claim 3, wherein each microelectrode of the at least one pair of microelectrodes has a width of about 50 microns.

5. The catheter of claim 4, wherein each microelectrode of the at least one pair of microelectrodes has an enlarged portion configured for electrical connection of its respective trace.

6. The catheter of claim 1, wherein each of the spines has a circular cross-section.

7. The catheter of claim 1, wherein each of the spines has a rectangular cross-section.

8. The catheter of claim 1, wherein the microelectrodes of the at least one pair of microelectrodes extend laterally on their respective spine.

9. The catheter of claim 1, wherein the soldering pad for each of the microelectrodes is located in the elongated body.

10. An electrophysiological catheter comprising:
an elongated body;
a distal electrode assembly comprising:
a plurality of spines, each of the spines having a free distal end and a proximal end extending from a distal end of the elongated body; and
a flexible panel on at least one of the spines, the flexible panel having a substrate conforming to an outer surface of its respective spine, a pair of microelectrodes, a trace for each of the microelectrodes, and a soldering pad for each of the microelectrodes, wherein each trace electrically couples a respective one of the microelectrodes and a respective one of the soldering pads, wherein the microelectrodes of the pair of microelectrodes are at least partially wrapped around their respective spine, and the microelectrodes of the pair of microelectrodes are separated by a space gap distance ranging between about 50-300 microns.

11. The catheter of claim 10, wherein each of the spines has a circular cross-section.

12. The catheter of claim 10, wherein each of the spines has a rectangular cross-section.

13. The catheter of claim 10, wherein each of the spines has a planar surface configured to contact a tissue surface.

14. The catheter of claim 13, wherein the pair of microelectrodes is positioned on the planar surface.

15. The catheter of claim 13, wherein the entirety of the pair of microelectrodes is within the planar surface.

16. The catheter of claim 10, wherein each microelectrode of the pair of microelectrodes has a width ranging between about 50-300 microns.

17. An electrophysiological catheter comprising:
an elongated body;
a distal electrode assembly comprising:
a plurality of spines, each of the spines having a free distal end and a proximal end extending from a distal end of the elongated body, each of the spines have a preformed inward curvature toward a longitudinal axis of the distal electrode assembly; and
a flexible panel on at least one of the spines, the flexible panel having a substrate conforming to an outer surface of its respective spine, a pair of microelectrodes, a trace for each of the microelectrodes, and a soldering pad for each of the microelectrodes, wherein each trace electrically couples a respective one of the microelectrodes and a respective one of the soldering pads, wherein the microelectrodes of the pair of microelectrodes are at least partially wrapped around their respective spine, and the microelectrodes of the pair of microelectrodes are separated by a space gap distance ranging between about 50-300 microns.

18. The catheter of claim 17, wherein the flexible panel has a longitudinal portion, at least a distal lateral portion, and a proximal base portion, wherein the trace for each of the microelectrodes is positioned in the longitudinal portion, the pair of microelectrodes is positioned in the distal lateral portion, and the soldering pad for each of the microelectrodes is positioned in the proximal base portion.

19. The catheter of claim 17, wherein the pair of microelectrodes is positioned on a planar surface of its respective spine.

20. The catheter of claim 17, wherein each of the spines has a rectangular cross section.

\* \* \* \* \*